US012097193B2

(12) United States Patent
Loewen et al.

(10) Patent No.: US 12,097,193 B2
(45) Date of Patent: Sep. 24, 2024

(54) METHODS FOR THE ADMINISTRATION OF COMT INHIBITORS

(71) Applicant: BIAL—PORTELA & CA, S.A., S. Mamede do Coronado (PT)

(72) Inventors: Gordon Loewen, Solano Beach, CA (US); Grace Liang, San Diego, CA (US); Evan Smith, Carlsbad, CA (US)

(73) Assignee: BIAL—PORTELA & CA, S.A., S. Mamede Do Coronado (PT)

(*) Notice: Subject to any disclaimer, the term of this patent is extended or adjusted under 35 U.S.C. 154(b) by 810 days.

(21) Appl. No.: 17/282,254

(22) PCT Filed: Oct. 4, 2019

(86) PCT No.: PCT/US2019/054670
§ 371 (c)(1),
(2) Date: Apr. 1, 2021

(87) PCT Pub. No.: WO2020/072886
PCT Pub. Date: Apr. 9, 2020

(65) Prior Publication Data
US 2021/0338651 A1 Nov. 4, 2021

Related U.S. Application Data

(60) Provisional application No. 62/811,068, filed on Feb. 27, 2019, provisional application No. 62/741,899, filed on Oct. 5, 2018.

(51) Int. Cl.
*A61K 31/4439* (2006.01)
*A61K 31/198* (2006.01)
*A61K 45/06* (2006.01)

(52) U.S. Cl.
CPC ........ *A61K 31/4439* (2013.01); *A61K 31/198* (2013.01); *A61K 45/06* (2013.01)

(58) Field of Classification Search
CPC ... A61K 31/4439; A61K 31/198; A61K 45/06
USPC ...................................................... 514/340
See application file for complete search history.

(56) References Cited

U.S. PATENT DOCUMENTS

| 8,168,793 | B2 | 5/2012 | Learmonth et al. |
| 8,524,746 | B2 | 9/2013 | Learmonth et al. |
| 8,536,203 | B2 | 9/2013 | Learmonth et al. |
| 8,907,099 | B2 | 12/2014 | Learmonth et al. |
| 9,126,988 | B2 | 9/2015 | Russo et al. |
| 9,132,094 | B2 | 9/2015 | Cardoso de Vasconcelos et al. |
| 9,446,012 | B2 | 9/2016 | Learmonth et al. |
| 9,550,759 | B2 | 1/2017 | Learmonth et al. |
| 9,630,955 | B2 | 4/2017 | Russo et al. |
| 9,745,290 | B2 | 8/2017 | Learmonth et al. |
| 10,065,944 | B2 | 9/2018 | Soares Da Silva et al. |
| 10,071,085 | B2 | 9/2018 | de Vasconcelos et al. |
| 10,336,740 | B2 | 7/2019 | Learmonth et al. |
| 10,357,468 | B2 | 7/2019 | Soares da Silva et al. |
| 10,583,130 | B2 | 3/2020 | de Vasconcelos et al. |
| 2010/0256194 | A1 | 10/2010 | Cardoso de Vasconcelos et al. |
| 2011/0301204 | A1 | 12/2011 | de Almeida et al. |
| 2013/0331416 | A1 | 12/2013 | Learmonth et al. |
| 2014/0045900 | A1 | 2/2014 | Soares Da Silva et al. |
| 2019/0008774 | A1 | 1/2019 | Cardoso de Vasconcelos et al. |
| 2019/0144436 | A1 | 5/2019 | Soares Da Silva et al. |
| 2020/0078328 | A1 | 3/2020 | Soares Da Silva et al. |
| 2020/0102295 | A1 | 4/2020 | Learmonth et al. |
| 2021/0023067 | A1 | 1/2021 | De Vasconcelos et al. |
| 2021/0186910 | A1 | 6/2021 | Soares Da Silva et al. |
| 2021/0220345 | A1 | 7/2021 | Loewen et al. |
| 2021/0315824 | A1 | 10/2021 | Cardoso de Vasconcelos et al. |
| 2022/0388999 | A1 | 12/2022 | Learmonth et al. |
| 2023/0147302 | A1 | 5/2023 | Vasconcelos et al. |
| 2023/0181474 | A1 | 6/2023 | Taniguchi et al. |
| 2023/0241046 | A1 | 8/2023 | Cardoso De Vasconcelos et al. |
| 2023/0355560 | A1 | 11/2023 | Soares Da Silva et al. |
| 2023/0390267 | A1 | 12/2023 | Soares Da Silva et al. |
| 2023/0398105 | A1 | 12/2023 | Vieira Araújo Soares Da Silva et al. |
| 2024/0000762 | A1 | 1/2024 | Soares Da Silva et al. |
| 2024/0066015 | A1 | 2/2024 | Soares Da Silva et al. |

FOREIGN PATENT DOCUMENTS

WO 2020072886 4/2020

OTHER PUBLICATIONS

U.S. Appl. No. 11/989,447, filed Jul. 26, 2006, U.S. Pat. No. 8,168,793, Issued.
U.S. Appl. No. 13/442,356, filed Apr. 9, 2012, U.S. Pat. No. 8,907,099, Issued.
U.S. Appl. No. 14/541,654, filed Nov. 14, 2014, U.S. Pat. No. 9,550,759, Issued.
U.S. Appl. No. 15/402,607, filed Jan. 10, 2017, U.S. Pat. No. 10,336,740, Issued.
U.S. Appl. No. 16/452,845, filed Jun. 26, 2019, 2020-0102295, Abandoned.
U.S. Appl. No. 17/694,902, filed Mar. 15, 2022, 2022-0388999, Published.
U.S. Appl. No. 13/002,287, filed Jul. 7, 2011, 2011-0301204, Abandoned.
U.S. Appl. No. 12/226,260, filed May 28, 2009, U.S. Pat. No. 8,536,203, Issued.
U.S. Appl. No. 14/014,548, filed Aug. 30, 2013, U.S. Pat. No. 9,446,012, Issued.
U.S. Appl. No. 12/524,848, filed Dec. 30, 2009, U.S. Pat. No. 8,524,746, Issued.
U.S. Appl. No. 13/950,661, filed Jul. 25, 2013, 2013-0331416, Abandoned.
U.S. Appl. No. 14/689,397, filed Apr. 17, 2015, U.S. Pat. No. 9,745,290, Issued.
U.S. Appl. No. 14/365,265, filed Jun. 13, 2014, U.S. Pat. No. 9,126,988, Issued.

(Continued)

*Primary Examiner* — Kristin A Vajda
(74) *Attorney, Agent, or Firm* — McCarter & English, LLP; Wei Song

(57) ABSTRACT

Provided are methods of administering a catechol-O-methyltransferase (COMT) inhibitor chosen from opicapone, or a pharmaceutically acceptable salt and/or isotopic variant thereof, to a patient in need thereof wherein the patient is already being administered quinidine or is suffering from a disease or disorder treatable by quinidine.

11 Claims, No Drawings

(56) References Cited

OTHER PUBLICATIONS

U.S. Appl. No. 14/814,603, filed Jul. 31, 2015, U.S. Pat. No. 9,630,955, Issued.
U.S. Appl. No. 15/528,886, filed May 23, 2017, U.S. Pat. No. 10,357,468, Issued.
U.S. Appl. No. 16/513,703, filed Jul. 17, 2019, 2020-0078328, Abandoned.
U.S. Appl. No. 17/010,601, filed Sep. 2, 2020, 2021-0186910, Abandoned.
U.S. Appl. No. 18/106,682, filed Feb. 7, 2023, 2023-0355560, Published.
U.S. Appl. No. 13/963,621, filed Aug. 9, 2013, U.S. Pat. No. 10,065,944, Issued.
U.S. Appl. No. 16/114,430, filed Aug. 28, 2018, 2019-0144436, Published.
U.S. Appl. No. 12/750,956, filed Mar. 31, 2010, U.S. Pat. No. 9,132,094, Issued.
U.S. Appl. No. 14/825,600, filed Aug. 13, 2015, U.S. Pat. No. 10,071,085, Issued.
U.S. Appl. No. 16/050,602, filed Jul. 31, 2018, U.S. Pat. No. 10,583,130, Issued.
U.S. Appl. No. 16/809,662, filed Mar. 5, 2020, 2021-0023067, Published.
U.S. Appl. No. 12/750,957, filed Mar. 31, 2010, 2010-0256194, Abandoned.
U.S. Appl. No. 16/122,643, filed Sep. 5, 2018, 2019-0008774, Abandoned.
U.S. Appl. No. 17/122,013, filed Dec. 15, 2020, 2021-0315824, Published.
U.S. Appl. No. 17/910,868, filed Sep. 12, 2022, 2023-0147302, Published.
U.S. Appl. No. 17/925,460, filed Nov. 15, 2022, 2023-0181474, Published.
U.S. Appl. No. 18/013,303, filed Dec. 28, 2022, 2023-0241046, Published.
U.S. Appl. No. 18/032,034, filed Apr. 14, 2023, 2023-0398105, Published.
U.S. Appl. No. 18/201,920, filed May 25, 2023, 2023-0390267, Published.
U.S. Appl. No. 18/370,005, filed Sep. 19, 2023, 2024-0000762, Published.
U.S. Appl. No. 18/273,515, filed Jul. 20, 2023, 2024-0066015, Published.
U.S. Appl. No. 17/220,367, filed Apr. 1, 2021, 2021-0220345, Published.
U.S. Appl. No. 13/583,375, filed Dec. 5, 2012, 2014-0045900, Abandoned.
Anonymous, EMA assessment report Ongentys (Opicapone) 2016, pp. 1-140. Retrieved from: https://www.ema.europa.eu/en/documents/assessment-report_en.pdf, retrieved on Jan. 7, 2020.
Anonymous: Pharmacokinetic-pharmacodynamic Interaction Between Each of Three Different Single Doses of BIA 9-1067 and a Single-dose of Controlled-release 100/25 mg Levodopa/Carbidopa, 2015, pp. 1-9. Retrieved from the Internet: URL:https://clinicaltrials.gov/ct2/show/st udy/NCT02169453, retrieved on Jan. 7, 2020.
Chin-Eng, Ong et al., The xenobiotic inhibitor pro le of cytochrome, Clin Pharmacol, vol. 50, Dec. 1, 2000 (Dec. 1, 2000), pp. 573-580.
International Application No. PCT/US2019/054670; International Search Report and Written Opinion of the International Searching Authority, date of mailing Jan. 27, 2020; 11 pages.

METHODS FOR THE ADMINISTRATION OF COMT INHIBITORS

This application claims the benefit of priority of U.S. Application Nos. 62/811,068, filed Feb. 27, 2019 and 62/741,899, filed Oct. 5, 2018, each of which is incorporated herein by reference in its entirety for all purposes.

Data from the Centers for Disease Control and Prevention's National Health and Nutrition Examination Survey indicate that about 20% of U.S. adults are taking three or more drugs. Among adults age 65 and older, 40% are taking five or more medications. Interactions between drugs can trigger unexpected pharmacological effects, including adverse drug events (ADEs), with causal mechanisms often unknown. Indeed, drug-drug interactions have been estimated to be associated with 30% of all of the reported ADEs.

Opicapone is a potent catechol-O-methyltransferase inhibitor which has the following chemical structure:

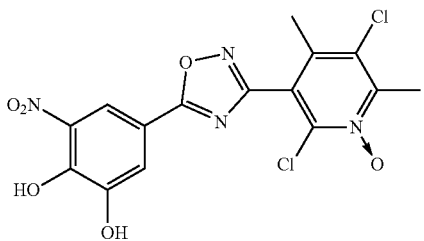 [SMILES: Cc1c(Cl)c(C)[n+]([O-])c(Cl)c1-c1noc(-c2cc(O)c(O)c([N+](=O)[O-])c2)n1]

A formulation of opicapone has been previously reported in the European approved drug label for ONGENTYS®. That label suggests that co-administration of opicapone with a drug which inhibits transporter-mediated clearance of opicapone will result in increased exposure to opicapone. i.e. a drug-drug interaction for opicapone:

In vitro studies have shown that opicapone is not transported by OATP1B1, but is transported by OATP1B3, and efflux transported by P-gp and BCRP. BIA 9-1103, its major metabolite, was transported by OATP1B1 and OATP1B3, and efflux transported by BCRP, but is not a substrate for the P-gp/MDR1 efflux transporter.

There is a significant, unmet need for methods for administering opicapone, to a patient in need thereof, wherein the patient also is being administered quinidine, which is a known P-gp inhibitor. The present disclosure fulfills these and other needs, as evident in reference to the following disclosure.

BRIEF SUMMARY

Provided is a method of administering a catechol-O-methyltransferase (COMT) inhibitor wherein the COMT inhibitor is opicapone, or a pharmaceutically acceptable salt and/or isotopic variant thereof, to a patient in need thereof, comprising: administering a therapeutically effective amount of the COMT inhibitor to the patient, and informing the patient or a medical care worker that co-administration of quinidine is not recommended.

Also provided is a method of administering a catechol-O-methyltransferase (COMT) inhibitor wherein the COMT inhibitor is opicapone, or a pharmaceutically acceptable salt and/or isotopic variant thereof, to a patient in need thereof wherein the patient is being treated with quinidine, comprising: discontinuing treatment of the quinidine and then administering a therapeutically effective amount of the COMT inhibitor to the patient, thereby avoiding the use of the COMT inhibitor in combination with quinidine.

Also provided is a method of treating Parkinson's disease and a disease or disorder treatable by quinidine, said method comprising: administering to a patient in need thereof, a therapeutically effective amount of opicapone, or a pharmaceutically acceptable salt and/or isotopic variant thereof and a therapeutically effective amount of a drug which is suitable for treating a disease or disorder treatable by quinidine, wherein said drug is not quinidine.

Also provided is a catechol-O-methyltransferase (COMT) inhibitor wherein the COMT inhibitor is opicapone, or a pharmaceutically acceptable salt and/or isotopic variant thereof, for use in a method of treating a neurological or psychiatric disease or disorder of a patient in need thereof, said method comprising: administering a therapeutically effective amount of the COMT inhibitor to the patient, and informing the patient or a medical care worker that co-administration of quinidine is not recommended.

Also provided is a catechol-O-methyltransferase (COMT) inhibitor wherein the COMT inhibitor is opicapone, or a pharmaceutically acceptable salt and/or isotopic variant thereof, for use in a method of treating a neurological or psychiatric disease or disorder of a patient in need thereof wherein the patient is being treated with quinidine, said method comprising: discontinuing treatment of the quinidine and then administering a therapeutically effective amount of the COMT inhibitor to the patient, thereby avoiding the use of the COMT inhibitor in combination with quinidine.

Also provided is a catechol-O-methyltransferase (COMT) inhibitor wherein the COMT inhibitor is opicapone, or a pharmaceutically acceptable salt and/or isotopic variant thereof, for use in a method of treating Parkinson's disease and a disease or disorder treatable by quinidine, said method comprising: administering to a patient in need thereof, a therapeutically effective amount of opicapone, or a pharmaceutically acceptable salt and/or isotopic variant thereof and a therapeutically effective amount of a drug which is suitable for treating a disease or disorder treatable by quinidine, wherein said drug is not quinidine.

Also provided is opicapone, or a pharmaceutically acceptable salt and/or isotopic variant thereof, and a drug which is suitable for treating a disease or disorder treatable by quinidine for use in the treatment of Parkinson's disease and a disease or disorder treatable by quinidine, wherein said drug is not quinidine itself.

Also provided is the use of a catechol-O-methyltransferase (COMT) inhibitor wherein the COMT inhibitor is opicapone, or a pharmaceutically acceptable salt and/or isotopic variant thereof, in the manufacture of a medicament for use in a method of treating a neurological or psychiatric disease or disorder of a patient in need thereof, said method comprising: administering a therapeutically effective amount of the COMT inhibitor to the patient, and informing the patient or a medical care worker that co-administration of quinidine is not recommended.

Also provided is the use of a catechol-O-methyltransferase (COMT) inhibitor wherein the COMT inhibitor is opicapone, or a pharmaceutically acceptable salt and/or isotopic variant thereof, in the manufacture of a medicament for use in a method of treating a neurological or psychiatric disease or disorder of a patient in need thereof wherein the patient is being treated with quinidine, said method comprising: discontinuing treatment of the quinidine and then administering a therapeutically effective amount of the COMT inhibitor to the patient, thereby avoiding the use of the COMT inhibitor in combination with quinidine.

Also provided is the use of opicapone, or a pharmaceutically acceptable salt and/or isotopic variant thereof, and a drug which is suitable for treating a disease or disorder treatable by quinidine, in the manufacture of a medicament for use in the treatment of Parkinson's disease and a disease or disorder treatable by quinidine, wherein said drug is not quinidine itself.

These and other aspects of the invention will be apparent upon reference to the following detailed description. To this end, various references are set forth herein which describe in more detail certain background information, procedures, compounds, and/or compositions, and are each hereby incorporated by reference in their entirety.

DETAILED DESCRIPTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" or "a certain embodiment" means that a particular feature, structure or characteristic described in connection with the embodiment is included in at least one embodiment. Thus, the appearances of the phrases "in one embodiment" or "in an embodiment" or "in some embodiments" or "in a certain embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise.

As used herein, "opicapone" may be referred to as 5-[3-(2,5-dichloro-4,6-dimethyl-1-oxy-pyridin-3-yl)-[1,2,4]oxadiazol-5-yl]-3-nitrobenzene-1,2-diol or as OPC or BIA 9-1067.

As used herein, "BIA 9-1103" means the compound which is an inactive metabolite of opicapone having the structure:

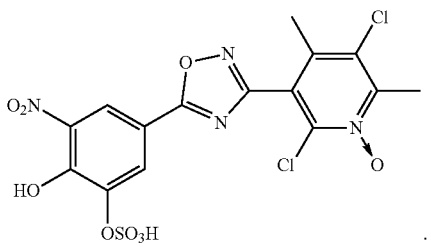

As used herein, "BIA 9-1079" means the compound which is an active metabolite of opicapone having the structure:

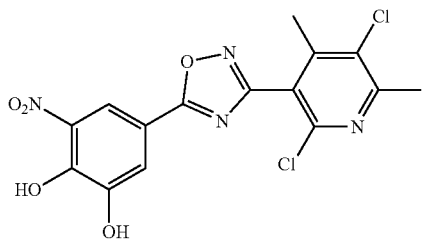

As used herein, "isotopic variant" means a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^{1}H$), deuterium ($^{2}H$), tritium, ($^{3}H$), carbon-11 ($^{11}C$), (14 carbon-12 ($^{12}C$), carbon-13 ($^{13}C$), carbon-14 ($^{14}C$), nitrogen-13 ($^{13}N$), nitrogen-14 ($^{14}N$) nitrogen-15 ($^{15}N$), oxygen-14 ($^{14}O$) oxygen-15 ($^{15}C$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$) iodine-125 ($^{125}I$) iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^{1}H$), deuterium ($^{2}H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), and oxygen-18 ($^{18}O$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^{3}H$), carbon-11 ($^{11}C$), carbon-14 ($^{14}C$), nitrogen-13 ($^{13}N$), oxygen-14 ($^{14}O$), and oxygen-15 ($^{15}O$). It will be understood that, in a compound as provided herein, any hydrogen can be $^{2}H$, as example, or any carbon can be $^{13}C$, as example, or any nitrogen can be $^{15}N$, as example, and any oxygen can be $^{18}O$, as example, where feasible according to the judgment of one of skill in the art. In certain embodiments, an "isotopic variant" of a compound contains an unnatural proportion of deuterium.

With regard to the compounds provided herein, when a particular atomic position is designated as having deuterium or "D" or "d", it is understood that the abundance of deuterium at that position is substantially greater than the natural abundance of deuterium, which is about 0.015%. A position designated as having deuterium typically has a minimum isotopic enrichment factor of, in certain embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position. The isotopic enrichment of the compounds provided herein can be determined using conventional analytical methods known to one of ordinary skill in the art, including mass spectrometry, nuclear magnetic resonance spectroscopy, and crystallography.

As used herein, "about" means±20% of the stated value, and includes more specifically values of ±10%, ±5%, ±2% and ±1% of the stated value.

As used herein, "AUC" refers to the area under the curve, or the integral, of the plasma concentration of an active pharmaceutical ingredient or metabolite over time following a dosing event.

As used herein "$AUC_{0-t}$" is the integral under the plasma concentration curve from time 0 (dosing) to time "t".

As used herein "$AUC_{0-tlast}$" is the integral under the plasma concentration curve from time 0 (dosing) to time of the last measurable concentration "tlast".

As used herein, "$AUC_{0-\infty}$" is the AUC from time 0 (dosing) to time infinity. Unless otherwise stated, AUC refers to $AUC_{0-\infty}$. Often a drug is packaged in a salt form and the dosage form strength refers to the mass of this salt form or the equivalent mass of the corresponding free base.

As used herein, $C_{max}$ is a pharmacokinetic parameter denoting the maximum observed blood plasma concentration following delivery of an active pharmaceutical ingredient. $C_{max}$ occurs at the time of maximum plasma concentration, $t_{max}$.

As used herein, "co-administer" and "co-administration" and variants thereof mean the administration of at least two drugs to a patient either subsequently, simultaneously, or consequently proximate in time to one another (e.g., within the same day, or week or period of 30 days, or sufficiently proximate that each of the at least two drugs can be simultaneously detected in the blood plasma). When co-administered, two or more active agents can be co-formulated as part of the same composition or administered as separate formulations. This also may be referred to herein as "concomitant" administration or variants thereof.

As used herein, "adjusting administration", "altering administration", "adjusting dosing", or "altering dosing" are all equivalent and mean tapering off, reducing or increasing the dose of the substance, ceasing to administer the substance to the patient, or substituting a different active agent for the substance.

As used herein, "administering to a patient" refers to the process of introducing a composition or dosage form into the patient via an art-recognized means of introduction.

As used herein the term "disorder" is intended to be generally synonymous, and is used interchangeably with, the terms "disease," "syndrome," and "condition" (as in medical condition), in that all reflect an abnormal condition of the human or animal body or of one of its parts that impairs normal functioning, is typically manifested by distinguishing signs and symptoms.

As used herein, a "dose" means the measured quantity of an active agent to be taken at one time by a patient. In certain embodiments, wherein the active agent is not opicapone free base, the quantity is the molar equivalent to the corresponding amount of opicapone free base.

As used herein, "dosing regimen" means the dose of an active agent taken at a first time by a patient and the interval (time or symptomatic) at which any subsequent doses of the active agent are taken by the patient such as from about 20 to about 160 mg once daily, e.g., about 20, about 40, about 60, about 80, about 100, about 120, or about 160 mg once daily. The additional doses of the active agent can be different from the dose taken at the first time.

As used herein, "effective amount" and "therapeutically effective amount" of an agent, compound, drug, composition or combination is an amount which is nontoxic and effective for producing some desired therapeutic effect upon administration to a subject or patient (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "informing" means referring to or providing published material, for example, providing an active agent with published material to a user; or presenting information orally, for example, by presentation at a seminar, conference, or other educational presentation, by conversation between a pharmaceutical sales representative and a medical care worker, or by conversation between a medical care worker and a patient; or demonstrating the intended information to a user for the purpose of comprehension.

As used herein, "labeling" means all labels or other means of written, printed, graphic, electronic, verbal, or demonstrative communication that is upon a pharmaceutical product or a dosage form or accompanying such pharmaceutical product or dosage form.

As used herein, "a "medical care worker" means a worker in the health care field who may need or utilize information regarding an active agent, including a dosage form thereof, including information on safety, efficacy, dosing, administration, or pharmacokinetics. Examples of medical care workers include physicians, pharmacists, physician's assistants, nurses, aides, caretakers (which can include family members or guardians), emergency medical workers, and veterinarians.

As used herein, "Medication Guide" means an FDA-approved patient labeling for a pharmaceutical product conforming to the specifications set forth in 21 CFR 208 and other applicable regulations which contains information for patients on how to safely use a pharmaceutical product. A medication guide is scientifically accurate and is based on, and does not conflict with, the approved professional labeling for the pharmaceutical product under 21 CFR 201.57, but the language need not be identical to the sections of approved labeling to which it corresponds. A medication guide is typically available for a pharmaceutical product with special risk management information.

As used herein, a "microparticulate formulation" means a pharmaceutical composition comprising opicapone, in a microparticulate form, such as can be formed by ball milling or by micronization through spiral jet mills. In some embodiments, a "microparticulate formulation" means a pharmaceutical composition comprising opicapone, wherein the opicapone is in a microparticulate form, such as can be formed by ball milling opicapone or by micronization of opicapone through spiral jet mills. Suitable micronization may be carried out with MCJETMILL type 200 milling equipment. In some embodiments, the D10 (EDC (equivalent circle diameter)) of the opicapone microparticles is not less than 3, 4, 5 or 6 μm (for example not less than 4 μm), the D50 (EDC) of the opicapone microparticles is 5-50, 10-45, 15-30 or 20-25 μm (for example 10-45 μm) and the D95 (EDC) of the opicapone microparticles is not more than 60, 70, 80 or 90 µm (for example not more than 90 µm). In some embodiments, the D10 (EDC) of the opicapone microparticles is not less than 4 or 5 µm (for example not less than 5 µm), the D50 (EDC) of the opicapone microparticles is 10-45 or 15-30 µm (for example 15-30 µm) and the D95 (EDC) of the opicapone microparticles is not more than 60 or 70 µm (for example not more than 60 µm). In some embodiments, the microparticles of opicapone comply with the following particle size specification (particle size determined by optical microscopy): D10 (EDC) is not less than 4 or 5 µm (for example not less than 5 µm), the D50 (EDC) is 10-45 or 15-30 µm (for example 15-30 µm) and the D95 (EDC) is not more than 60 or 70 µm (for example not more than 60 µm). See, e.g., U.S. Pat. No. 9,126,988, which is incorporated herein by reference in its entirety for all purposes. In some embodiments, the microparticulate formulation also comprises the following excipients: lactose monohydrate; sodium starch glycolate, such as Type A; maize starch, such as pregelatinized; and magnesium stearate.

As used herein, "patient" or "individual" or "subject" means a mammal, including a human, for whom or which therapy is desired, and generally refers to the recipient of the therapy.

As used herein, "patient package insert" means information for patients on how to safely use a pharmaceutical product that is part of the FDA-approved labeling. It is an extension of the professional labeling for a pharmaceutical product that may be distributed to a patient when the product is dispensed which provides consumer-oriented information about the product in lay language, for example it may describe benefits, risks, how to recognize risks, dosage, or administration.

As used herein, "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, a "product" or "pharmaceutical product" means a dosage form of an active agent plus published material, and optionally packaging.

As used herein, "product insert" means the professional labeling (prescribing information) for a pharmaceutical product, a patient package insert for the pharmaceutical product, or a medication guide for the pharmaceutical product.

As used herein, "professional labeling" or "prescribing information" means the official description of a pharmaceutical product approved by a regulatory agency (e.g., FDA or EMEA) regulating marketing of the pharmaceutical product, which includes a summary of the essential scientific information needed for the safe and effective use of the drug, such as, for example indication and usage; dosage and administration; who should take it; adverse events (side effects); instructions for use in special populations (pregnant women, children, geriatric, etc.); safety information for the patient, and the like.

As used herein, "published material" means a medium providing information, including printed, audio, visual, or electronic medium, for example a flyer, an advertisement, a product insert, printed labeling, an internet web site, an internet web page, an internet pop-up window, a radio or television broadcast, a compact disk, a DVD, an audio recording, or other recording or electronic medium.

As used herein, "risk" means the probability or chance of adverse reaction, injury, or other undesirable outcome arising from a medical treatment. An "acceptable risk" means a measure of the risk of harm, injury, or disease arising from a medical treatment that will be tolerated by an individual or group. Whether a risk is "acceptable" will depend upon the advantages that the individual or group perceives to be obtainable in return for taking the risk, whether they accept whatever scientific and other advice is offered about the magnitude of the risk, and numerous other factors, both political and social. An "acceptable risk" of an adverse reaction means that an individual or a group in society is willing to take or be subjected to the risk that the adverse reaction might occur since the adverse reaction is one whose probability of occurrence is small, or whose consequences are so slight, or the benefits (perceived or real) of the active agent are so great. An "unacceptable risk" of an adverse reaction means that an individual or a group in society is unwilling to take or be subjected to the risk that the adverse reaction might occur upon weighing the probability of occurrence of the adverse reaction, the consequences of the adverse reaction, and the benefits (perceived or real) of the active agent. "At risk" means in a state or condition marked by a high level of risk or susceptibility. Risk assessment consists of identifying and characterizing the nature, frequency, and severity of the risks associated with the use of a product.

As used herein, "safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

As used herein, "$t_{max}$" is a pharmacokinetic parameter denoting the time to maximum blood plasma concentration following delivery of an active pharmaceutical ingredient As used herein, "$t_{1/2}$" or "plasma half-life" or "elimination half-life" or the like is a pharmacokinetic parameter denoting the apparent plasma terminal phase half-life, i.e., the time, after absorption and distribution of a drug is complete, for the plasma concentration to fall by half.

As used herein, "treating" or "treatment" refers to therapeutic applications to slow or stop progression of a disorder, prophylactic application to prevent development of a disorder, and/or reversal of a disorder. Reversal of a disorder differs from a therapeutic application which slows or stops a disorder in that with a method of reversing, not only is progression of a disorder completely stopped, cellular behavior is moved to some degree, toward a normal state that would be observed in the absence of the disorder.

As used herein, "treatable" refers to an expected ability of an agent to treat a disorder based on knowledge available to a person of ordinary skill in the relevant medical art, for example, knowledge that the agent has been used to treat a disorder and/or that the agent exhibits a biological effect which is beneficial for treating the disorder.

As used herein, "COMT" refers to catechol-O-methyltransferase, which is one of several enzymes that degrade catecholamines (such as dopamine, epinephrine, and norepinephrine), catecholestrogens, and various drugs and substances having a catechol structure. In humans, the catechol-O-methyltransferase protein is encoded by the COMT gene. Two isoforms of COMT are produced: the soluble short form (S-COMT) and the membrane bound long form (MB-COMT).

As used herein, the term "COMT inhibitor", "inhibit COMT", or "inhibition of COMT" refers to the ability of a compound disclosed herein to alter the function of COMT. A COMT inhibitor may block or reduce the activity of COMT by forming a reversible or irreversible covalent bond between the inhibitor and COMT or through formation of a noncovalently bound complex. Such inhibition may be manifest only in particular cell types or may be contingent on a particular biological event. The term "COMT inhibitor", "inhibit COMT", or "inhibition of COMT" also refers to altering the function of COMT by decreasing the probability that a complex forms between a COMT and a natural substrate.

Provided is a method of administering a catechol-O-methyltransferase (COMT) inhibitor wherein the COMT inhibitor is opicapone, or a pharmaceutically acceptable salt and/or isotopic variant thereof, to a patient in need thereof, comprising: administering a therapeutically effective amount of the COMT inhibitor to the patient, and informing the patient or a medical care worker that co-administration of quinidine is not recommended.

In some embodiments, the patient or medical care worker is informed that co-administration of quinidine should be avoided or discontinued.

Also provided is a method of administering a catechol-O-methyltransferase (COMT) inhibitor wherein the COMT inhibitor is opicapone, or a pharmaceutically acceptable salt and/or isotopic variant thereof, to a patient in need thereof wherein the patient is being treated with quinidine, comprising: discontinuing treatment of the quinidine and then administering a therapeutically effective amount of the COMT inhibitor to the patient, thereby avoiding the use of the COMT inhibitor in combination with quinidine.

In some embodiments, the method further comprises administering to the patient a drug which is suitable for treating a disease or disorder treatable by quinidine, wherein said drug is not quinidine.

Also provided is a method of treating Parkinson's disease and a disease or disorder treatable by quinidine, said method comprising: administering to a patient in need thereof, a therapeutically effective amount of opicapone, or a pharmaceutically acceptable salt and/or isotopic variant thereof and a therapeutically effective amount of a drug which is suitable for treating a disease or disorder treatable by quinidine, wherein said drug is not quinidine.

In some embodiments, the patient is, or was, being administered quinidine for treatment of arrhythmia, malaria, or pseudobulbar affect.

In some embodiments, the patient is, or was, being administered quinidine for treatment of arrhythmia. In some embodiments, the drug which is suitable for treating a disease or disorder treatable by quinidine is chosen from disopyramide, procainamide, lidocaine, mexiletine, flecainide, propafenone, acebutolol, atenolol, betaxolol, bisoprolol, carvedilol, esmolol, metoprolol, nadolol, propranolol, timolol, amiodarone, azimilde, bretylium, dofetilide, dronedarone, ibutilide, sotalol, vernakalant, diltiazem, verapamil, adenosine, and digoxin. In some embodiments, the drug which is suitable for treating a disease or disorder treatable by quinidine is chosen from disopyramide and procainamide.

In some embodiments, the patient is, or was, being administered quinidine for treatment of malaria. In some embodiments, the drug which is suitable for treating a disease or disorder treatable by quinidine is chosen from an anti-malarial other than quinidine. In some embodiments, the anti-malarial is chosen from atovaquone-proguanil, primaquine phosphate, mefloquine and combinations thereof.

In some embodiments, the patient is, or was, being administered quinidine for treatment of pseudobulbar affect. In some embodiments, the patient is, or was, being administered quinidine in combination with dextromethorphan, deudextromethorphan, or a salt thereof for treatment of pseudobulbar affect. In some embodiments, the drug which is suitable for treating a disease or disorder treatable by quinidine is an antidepressant.

In some embodiments, the COMT inhibitor is administered to the patient to treat a central or peripheral nervous system associated disorder. In some embodiments, the central or peripheral nervous system associated disorder is chosen from movement disorders and schizoaffective disorders.

In some embodiments, the movement disorder is chosen from Parkinson's disease and parkinsonian disorders, dystonia, dyskinesia, extrapyramidal syndromes, gait, tremor, chorea, ballism, akathisia, athetosis, bradykinesia, freezing, rigidity, postural instability, myoclonus, restless legs syndrome, tics, Tourette syndrome, and peripheral diseases associated with amyloidosis. In some embodiments, the movement disorder is chosen from Parkinson's disease, dystonia, dyskinesia, and extrapyramidal syndromes. In some embodiments, the movement disorder is Parkinson's disease.

In some embodiments, the movement disorder is treatable by L-DOPA and/or AADC therapy. In some embodiments, the method further comprises the step of administering an AADC inhibitor to the patient. In some embodiments, the patient is receiving therapy with L-DOPA or an AADC inhibitor or both L-DOPA and an AADC inhibitor. In some embodiments, the method further comprises the step of administering L-DOPA and an AADC inhibitor to the patient either concomitantly or sequentially with the opicapone. In some embodiments, the method further comprises the step of administering L-DOPA and an AADC inhibitor to the patient separately with the opicapone. In some embodiments, the method further comprises the step of administering L-DOPA to the patient.

In some embodiments, the method further comprises the step of monitoring the patient for one or more exposure-related adverse reactions related to the administration of the L-DOPA. In some embodiments, the method further comprises reducing the amount of the L-DOPA based on the patient's ability to tolerate one or more of the exposure-related adverse reactions.

In some embodiments, the administration of the COMT inhibitor is once daily. In some embodiments, the administration of the COMT inhibitor is once every other day.

In some embodiments, the administration of the COMT inhibitor is in the morning, mid-day, noon, afternoon, evening, or midnight. In some embodiments, the administration of the COMT inhibitor is in the evening.

In some embodiments, the COMT inhibitor is administered orally.

In some embodiments, the COMT inhibitor is administered in the form of a tablet or capsule.

In some embodiments, the COMT inhibitor is administered with or without food. In some embodiments, the COMT inhibitor is administered without food. In some embodiments, the COMT inhibitor is administered with food.

In some embodiments, the COMT inhibitor is opicapone or a pharmaceutically acceptable salt thereof. In some embodiments, the COMT inhibitor is an isotopic variant of opicapone or a pharmaceutically acceptable salt thereof. In some embodiments, the COMT inhibitor is opicapone. In some embodiments, the COMT inhibitor is an isotopic variant of opicapone.

In some embodiments, the opicapone or a pharmaceutically acceptable salt thereof is administered in an amount equivalent to about 25 mg of opicapone free base. In some embodiments, the opicapone or a pharmaceutically acceptable salt thereof is administered in an amount equivalent to about 50 mg of opicapone free base.

Opicapone can be prepared according to WO 2007/013830, WO 2008/094053, and WO 2013/089573, the disclosure of each of which is incorporated herein by reference in its entirety. In some embodiments, the COMT inhibitor is administered as a microparticulate formulation.

Also provided is a kit comprising:
 a pharmaceutical composition of a catechol-O-methyltransferase (COMT) inhibitor wherein the COMT inhibitor is opicapone, or a pharmaceutically acceptable salt and/or isotopic variant thereof; and
 a patient package insert, wherein the patient package insert includes a warning with respect to co-administration of the COMT inhibitor and quinidine.

Also provided is a catechol-O-methyltransferase (COMT) inhibitor wherein the COMT inhibitor is opicapone, or a pharmaceutically acceptable salt and/or isotopic variant thereof, for use in a method of treating a neurological or psychiatric disease or disorder of a patient in need thereof, said method comprising: administering a therapeutically effective amount of the COMT inhibitor to the patient, and informing the patient or a medical care worker that co-administration of quinidine is not recommended.

Also provided is a catechol-O-methyltransferase (COMT) inhibitor wherein the COMT inhibitor is opicapone, or a pharmaceutically acceptable salt and/or isotopic variant thereof, for use in a method of treating a neurological or psychiatric disease or disorder of a patient in need thereof wherein the patient is being treated with quinidine, said method comprising: discontinuing treatment of the quinidine and then administering a therapeutically effective amount of the COMT inhibitor to the patient, thereby avoiding the use of the COMT inhibitor in combination with quinidine.

Also provided is a catechol-O-methyltransferase (COMT) inhibitor wherein the COMT inhibitor is opicapone, or a pharmaceutically acceptable salt and/or isotopic variant thereof, for use in a method of treating Parkinson's disease and a disease or disorder treatable by quinidine, said method comprising: administering to a patient in need thereof, a therapeutically effective amount of opicapone, or a pharmaceutically acceptable salt and/or isotopic variant thereof and a therapeutically effective amount of a drug which is suitable for treating a disease or disorder treatable by quinidine, wherein said drug is not quinidine.

Also provided is opicapone, or a pharmaceutically acceptable salt and/or isotopic variant thereof, and a drug which is suitable for treating a disease or disorder treatable by quinidine for use in the treatment of Parkinson's disease and a disease or disorder treatable by quinidine, wherein said drug is not quinidine itself.

Also provided is the use of a catechol-O-methyltransferase (COMT) inhibitor wherein the COMT inhibitor is opicapone, or a pharmaceutically acceptable salt and/or isotopic variant thereof, in the manufacture of a medicament for use in a method of treating a neurological or psychiatric disease or disorder of a patient in need thereof, said method comprising: administering a therapeutically effective amount of the COMT inhibitor to the patient, and informing the patient or a medical care worker that co-administration of quinidine is not recommended.

Also provided is the use of a catechol-O-methyltransferase (COMT) inhibitor wherein the COMT inhibitor is opicapone, or a pharmaceutically acceptable salt and/or isotopic variant thereof, in the manufacture of a medicament for use in a method of treating a neurological or psychiatric disease or disorder of a patient in need thereof wherein the patient is being treated with quinidine, said method comprising: discontinuing treatment of the quinidine and then administering a therapeutically effective amount of the COMT inhibitor to the patient, thereby avoiding the use of the COMT inhibitor in combination with quinidine.

Also provided is the use of opicapone, or a pharmaceutically acceptable salt and/or isotopic variant thereof, and a drug which is suitable for treating a disease or disorder treatable by quinidine, in the manufacture of a medicament for use in the treatment of Parkinson's disease and a disease or disorder treatable by quinidine, wherein said drug is not quinidine itself.

Pharmaceutical Compositions

Also provided herein is a pharmaceutical composition for use in treating neurological or psychiatric diseases or disorders, comprising the COMT inhibitor as an active pharmaceutical ingredient, in combination with one or more pharmaceutically acceptable carriers or excipients. The pharmaceutically acceptable carriers or excipients may be either solid or liquid. Solid form preparations include powders, tablets, dispersible granules and capsules. A solid carrier can be one or more substances which may also act as diluents, flavouring agents, solubilizers, lubricants, suspending agents, binders or tablet disintegrating agents; it may also be an encapsulating material.

In some embodiments, the pharmaceutical composition is in unit dosage form, e.g. packaged preparation, the package containing discrete quantities of preparation such as packeted tablets, capsules and powders in vials or ampoules. In some embodiments, the unit dosage form is a tablet or a capsule. See, e.g., U.S. Pat. No. 10,065,944, which is incorporated herein by reference for all purposes.

Capsules include, but are not limited to, gelatin capsules and hydroxypropylmethyl cellulose (hypromellose) capsules. Suitable methods for filling such capsules with a composition according to an embodiment of the disclosure are well-known to those of skill in the art.

Tablets may be formed by any method known to those of skill in the art such as compression. In some embodiments, tablets may be coated, for example with aqueous based film-coatings, solvent based film-coatings and/or sugar coatings.

The compositions may also be colored, for example by inclusion of a coloring in the composition, or by coating the composition or formulation.

In some embodiments, the COMT inhibitor may be present in granular form.

In some embodiments, the pharmaceutical composition comprises the COMT inhibitor as an active pharmaceutical ingredient, in combination with, at least one phosphate derivative, and at least one polyvinylpyrrolidone derivative compound; wherein said at least one active pharmaceutical ingredient is present in the composition in granular form and wherein the bulk density of the composition is greater than 0.2 g/mL. See, e.g., U.S. Pat. No. 9,132,094, which is incorporated herein by reference for all purposes.

In some embodiments when the COMT inhibitor is granular, the at least one phosphate derivative and the at least one PVP derivative compound may, independently, be intragranular, extragranular, or part intragranular and part extragranular. In some embodiments, the compositions may exhibit a bulk density that is greater than that of the API alone, and that may, in some embodiments, be significantly increased. In some embodiments, the compositions may exhibit good flowability, that may, in some embodiments, be significantly improved over that of the COMT inhibitor alone.

In some embodiments, the pharmaceutical composition comprises granules comprising the COMT inhibitor, wherein the composition has a bulk density greater than 0.2 g/mL. See, e.g., U.S. Pat. No. 10,071,085, which is incorporated herein by reference for all purposes.

In some embodiments, the pharmaceutical composition is any one of the compositions disclosed in US2010/0256194 A1, which is incorporated herein by reference for all purposes.

In some embodiments, the pharmaceutical composition in unit dosage form for oral administration comprises a COMT inhibitor in microparticulate form having a particular size specification with D10 equivalent circle diameter not less than 4 μm, a D50 equivalent circle diameter of 10-45 μm and a D95 equivalent circle diameter of not more than 80 μm and a pharmaceutically acceptable carrier thereof. See, e.g., U.S. Pat. No. 9,630,955, which is incorporated herein by reference for all purposes.

In some embodiments, the COMT inhibitor employed in such compositions is microparticulate, for example as formed by ball milling or by micronization through spiral jet mills. Suitable micronization may be carried out with MCJETMILL type 200 milling equipment. In some embodiments, the D10 (EDC (equivalent circle diameter)) of the COMT inhibitor is not less than 3, 4, 5 or 6 μm (for example not less than 4 μm), the D50 (EDC) of the COMT inhibitor is 5-50, 10-45, 15-30 or 20-25 μm (for example 10-45 μm) and the D95 (EDC) of the COMT inhibitor is not more than 60, 70, 80 or 90 μm (for example not more than 90 μm). In some embodiments, the D10 (EDC) of the COMT inhibitor is not less than 4 or 5 μm (for example not less than 5 μm), the D50 (EDC) of the COMT inhibitor is 10-45 or 15-30 μm (for example 15-30 μm) and the D95 (EDC) of the COMT inhibitor is not more than 60 or 70 μm (for example not more than 60 μm).

In some embodiments, the pharmaceutical composition is a stable composition comprising: a COMT inhibitor; at least one filler; and at least one binder; wherein at least the at least one active pharmaceutical ingredient is present in the composition in granular form. In some embodiments, the compositions may also comprise at least one filler and at least one binder. In some embodiments, the filler may not be a phosphate derivative and/or the binder may not be a polyvinylpyrrolidone derivative compound. In some embodiments when the COMT inhibitor is granular, the at least one filler and at least one binder may, independently, be intragranular, extragranular, or part intragranular and part extragranular. In some embodiments, the compositions may exhibit a bulk density that is greater than that of the COMT inhibitor alone, and that may, in some embodiments, be a significantly increased. The compositions may also exhibit improvements in other characteristics such as compressibility. Use of the methods described herein may also result in improvements in the granule properties of the compositions such as improved granule size and uniformity of granule size and/or of granule mass. In some embodiments, the compositions may be stable over time, and may, in some embodiments exhibit enhanced stability. See, e.g., US 2010/0256194, which is incorporated herein by reference for all purposes.

In some embodiments, the compositions may comprise a further active pharmaceutical ingredient, for example the compositions may comprise, in addition to the COMT inhibitor, further active pharmaceutical ingredients such as L-DOPA, a peripheral amino acid decarboxylase (AADC) inhibitor, such as carbidopa or benserazide.

Examples of embodiments of the present disclosure are provided in the following examples. The following examples are presented only by way of illustration and to assist one of ordinary skill in using the disclosure. The examples are not intended in any way to otherwise limit the scope of the disclosure.

EXAMPLES

Example 1

A Phase 1, Randomized, Open-Label, Two-Period Crossover Study to Assess the Effect of Quinidine on the Pharmacokinetics of Opicapone (OPC) in Healthy Subjects This was a Phase 1, randomized, open-label, 2-period crossover drug interaction study of the effect of quinidine on the PK of OPC in healthy subjects. A total of 20 subjects (10 males and 10 females) were randomized to 1 of 2 treatment sequences (5 males and 5 females per sequence) as depicted in the table below. Randomization to treatment sequence were stratified by gender. Enrolled subjects received a single dose of each of the following treatments under fasted conditions: OPC 50 mg and quinidine 600 mg plus OPC 50 mg (OPC will be administered 1 hour after quinidine). There was be a 14-day washout between the doses in each treatment period.

| Treatment Sequence | Treatment Period 1 | Treatment Period 2 |
| --- | --- | --- |
| 1 | OPC 50 mg | Quinidine 600 mg + OPC 50 mg |
| 2 | Quinidine 600 mg + OPC 50 mg | OPC 50 mg |

Subjects fasted overnight for at least 10 hours before OPC dosing on Day 1 and continued to fast for an additional 4 hours after OPC dosing. On the morning of Day 1, subjects were dosed with OPC 50 mg or quinidine 600 mg plus OPC 50 mg (depending on their assigned randomized treatment sequence), and had serial PK blood samples collected.

Blood samples for the assessment of plasma concentrations of OPC and its metabolites were collected within 30 minutes predose and approximately 0.5, 1, 1.5, 2, 3, 4, 6, 8, 10, 12, 24, 48, 72, 96, and 120 hours postdose. The PK parameters to be calculated included the following for OPC and its metabolites:

Blood samples for the assessment of plasma concentrations of OPC and its metabolites were collected within 30 minutes predose and approximately 0.5, 1, 1.5, 2, 3, 4, 6, 8, 10, 12, 24, 48, 72, 96, and 120 hours postdose. The PK parameters to be calculated included the following for OPC and its metabolites:

Area under the plasma concentration versus time curve from 0 hours to last measurable concentration ($AUC_{0-tlast}$).

Area under the plasma concentration versus time curve from 0 hours extrapolated to infinity ($AUC_{0-\infty}$).

Maximum plasma concentration ($C_{max}$).

Time to maximum plasma concentration ($t_{max}$).

Time to first measurable concentration ($T_{lag}$).

Apparent terminal half-life ($t_{1/2}$).

Apparent terminal rate constant ($\lambda_z$).

Apparent mean residence time (MRT).

Molar ratio of the metabolites to the parent drug OPC.

The following plasma PK parameters were calculated only for OPC:

Apparent systemic clearance after oral administration (CL/F).

Apparent volume of distribution during the terminal phase after oral administration (Vz/F).

PK parameters for OPC and its metabolites were calculated using noncompartmental methods. The 90% confidence intervals (CIs) about the geometric mean ratios of $AUC_{0-tlast}$, $AUC_{0-\infty}$, and $C_{max}$ for OPC administered with quinidine (Test) versus OPC administered alone (Reference) were calculated along with descriptive statistics for all PK parameters and plasma concentrations. Safety data will be summarized with descriptive statistics. A summary of those results are provided below.

| Summary of Opicapone Plasma Pharmacokinetic Parameters (PK Population) | | | | | | | |
|---|---|---|---|---|---|---|---|
| Treatment | Statistic | Cmax (ng/mL) | Tmax (h) | Tlag (h) | t½ (h) | AUC(0-inf) (h*ng/mL) | AUC(0-last) (h*ng/mL) |
| OPC | n | 18 | 18 | 18 | 16 | 16 | 18 |
|  | Mean | 804.3 |  |  | 0.9184 | 2136 | 2045 |
|  | SD | 255.0 |  |  | 0.2636 | 571.5 | 573.8 |
|  | Median | 782.4 | 1.53 | 0.00 | 0.9317 | 2019 | 1938 |
|  | Min | 399.7 | 1.00 | 0.00 | 0.5900 | 996.5 | 900.1 |
|  | Max | 1327 | 4.00 | 0.50 | 1.640 | 3299 | 3280 |
|  | CV | 31.71 |  |  | 28.70 | 26.76 | 28.05 |
|  | Geometric Mean | 765.9 |  |  | 0.8865 | 2057 | 1965 |
|  | Geometric CV | 33.54 |  |  | 27.63 | 29.86 | 30.90 |
| Quinidine + OPC | n | 18 | 18 | 18 | 6 | 6 | 18 |
|  | Mean | 569.0 |  |  | 0.9185 | 1744 | 1327 |
|  | SD | 197.9 |  |  | 0.2649 | 496.0 | 478.9 |
|  | Median | 562.1 | 3.00 | 0.50 | 0.8797 | 1854 | 1210 |
|  | Min | 221.3 | 1.50 | 0.00 | 0.6562 | 823.3 | 470.4 |
|  | Max | 995.5 | 4.00 | 1.52 | 1.331 | 2224 | 2199 |
|  | CV | 34.78 |  |  | 28.84 | 28.45 | 36.08 |
|  | Geometric Mean | 535.3 |  |  | 0.8881 | 1665 | 1238 |
|  | Geometric CV | 38.36 |  |  | 28.78 | 37.36 | 41.64 | n: number of subjects analyzed in each parameter(PK Population);

SD: standard deviation;

CV %: coefficient of variation;

Geometric CV = 100 × [exp (s^2)−1]^½, where s is the standard deviation of the data on a log scale.

A statistical assessment of the drug-drug interaction between quinidine and opicapone is provided below. Pharmacokinetic parameters (AUC0-inf, AUC0-t, and Cmax) for Opicapone were natural log-transformed prior to analysis and evaluated separately using a linear mixed effects model with fixed effects terms for sequence, period, and treatment. In this analysis, subject nested within sequence was considered a random effect Geometric means (GM), ratio of geometric means (GMR), and their confidence intervals (CI) are shown on the original scale of measurement. CV %=SQRT[exp($s^2$)−1]×100 and 's' is the standard deviation of the log-transformed values.

| Parameter | Opicapone | | | Quinidine + Opicapone | | | Quinidine + Opicapone / Opicapone | | CV (%) |
|---|---|---|---|---|---|---|---|---|---|
| | N [1] | GM | 95% CI | N [1] | GM | 95% CI | GMR | 90% CI | |
| AUC0-inf (h · ng/mL) | 16 | 2030 | (1746.31, 2359.58) | 6 | 1399 | (1097.80, 1781.66) | 0.69 | (0.55, 0.86) | 14.59 |
| AUC0-t (h · ng/mL) | 18 | 1965 | (1654.47, 2332.68) | 18 | 1238 | (1042.66, 1470.07) | 0.63 | (0.54, 0.73) | 26.75 |
| Cmax (ng/mL) | 18 | 765.9 | (644.97, 909.47) | 18 | 535.3 | (450.75, 635.60) | 0.70 | (0.60, 0.82) | 27.67 |

[1] Shows the number of subjects exposed to each treatment that were used in the mixed model.

Those results show that there was an approximately 30% decrease in opicapone exposure in those patients who were also being administered quinidine.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of administering a catechol-O-methyltransferase (COMT) inhibitor wherein the COMT inhibitor is opicapone, or a pharmaceutically acceptable salt and/or isotopic variant thereof, to a patient in need thereof wherein the patient is being treated with quinidine, comprising:
   discontinuing treatment of the quinidine and then
   administering a therapeutically effective amount of the COMT inhibitor to the patient,
   thereby avoiding the use of the COMT inhibitor in combination with quinidine.

2. The method of claim 1, further comprising administering to the patient a drug which is suitable for treating a disease or disorder treatable by quinidine, wherein said drug is not quinidine.

3. The method of claim 2, wherein the patient is, or was, being administered quinidine for treatment of arrhythmia, malaria, or pseudobulbar affect.

4. The method of claim 3, wherein the patient is, or was, being administered quinidine for treatment of arrhythmia.

5. The method of claim 4, wherein the drug which is suitable for treating a disease or disorder treatable by quinidine is chosen from disopyramide, procainamide, lidocaine, mexiletine, flecainide, propafenone, acebutolol, atenolol, betaxolol, bisoprolol, carvedilol, esmolol, metoprolol, nadolol, propranolol, timolol, amiodarone, azimilde, bretylium, dofetilide, dronedarone, ibutilide, sotalol, vernakalant, diltiazem, verapamil, adenosine, and digoxin.

6. The method of claim 5, wherein the drug which is suitable for treating a disease or disorder treatable by quinidine is chosen from disopyramide and procainamide.

7. The method of claim 3, wherein the patient is, or was, being administered quinidine for treatment of malaria.

8. The method of claim 7, wherein the drug which is suitable for treating a disease or disorder treatable by quinidine is chosen from an anti-malarial other than quinidine.

9. The method of claim 8, wherein the anti-malarial is chosen from atovaquone-proguanil, primaquine phosphate, mefloquine and combinations thereof.

10. The method of claim 3, wherein the patient is, or was, being administered quinidine for treatment of pseudobulbar affect.

11. The method of claim 10, wherein the drug which is suitable for treating a disease or disorder treatable by quinidine is an antidepressant.

* * * * *